(12) United States Patent
Ogawa et al.

(10) Patent No.: US 12,741,097 B2
(45) Date of Patent: Sep. 22, 2026

(54) CONNECTION STRUCTURE AND LIQUID MEDICINE ADMINISTRATION TOOL

(71) Applicant: TERUMO KABUSHIKI KAISHA, Tokyo (JP)

(72) Inventors: Junichi Ogawa, Yamanashi (JP); Kentaro Nakajima, Yamanashi (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 1084 days.

(21) Appl. No.: 17/483,117

(22) Filed: Sep. 23, 2021

(65) Prior Publication Data

US 2022/0008656 A1 Jan. 13, 2022

Related U.S. Application Data

(63) Continuation of application No. PCT/JP2020/006454, filed on Feb. 19, 2020.

(30) Foreign Application Priority Data

Mar. 26, 2019 (JP) ................................ 2019-058721

(51) Int. Cl.
*A61M 5/24* (2006.01)
*A61J 1/14* (2023.01)
(Continued)

(52) U.S. Cl.
CPC .......... *A61M 5/2459* (2013.01); *A61J 1/1412* (2013.01); *A61J 1/201* (2015.05);
(Continued)

(58) Field of Classification Search
CPC .............. A61M 5/2455; A61M 5/2459; A61M 5/2466; A61M 5/343; A61M 5/344;
(Continued)

(56) References Cited

U.S. PATENT DOCUMENTS 2,752,919 A 7/1956 Daniel
5,624,402 A 4/1997 Imbert
(Continued)

FOREIGN PATENT DOCUMENTS

JP H08215307 A 8/1996
JP 2010131064 A 6/2010
WO 2018168989 A1 9/2018

OTHER PUBLICATIONS

International Search Report (PCT/ISA/210) with translation and Written Opinion (PCT/ISA/237) mailed on Apr. 28, 2020, by the Japanese Patent Office as the International Searching Authority for International Application No. PCT/JP2020/006454.

(Continued)

*Primary Examiner* — Michael J Tsai
*Assistant Examiner* — Forrest B Dipert
(74) *Attorney, Agent, or Firm* — BUCHANAN INGERSOLL & ROONEY PC

(57) ABSTRACT

A connection structure of a medical container includes a liquid medicine containing part that contains a liquid medicine and a liquid medicine discharge part that discharges the liquid medicine includes: a sealing member including a mounting part to be mounted to cover the outside of the liquid medicine discharge part, an opening formed in the mounting part in an extending direction of the liquid medicine discharge part, and an elastic sealing body disposed in a space between the opening and the liquid medicine discharge part and sealing the liquid medicine discharge part; and a connector including a connection needle that punctures the elastic sealing body, and a needle hub that holds the connection needle, in which the connector has a push-in structure that compresses the elastic sealing body when the connection needle punctures the elastic sealing body.

19 Claims, 10 Drawing Sheets

(51) Int. Cl.

*A61J 1/20* (2006.01)
*A61M 5/162* (2006.01)
*A61M 5/34* (2006.01)
*A61M 39/10* (2006.01)
*A61M 39/14* (2006.01)

(52) U.S. Cl.

CPC ............ *A61M 5/162* (2013.01); *A61M 5/343* (2013.01); *A61M 5/345* (2013.01); *A61M 39/14* (2013.01); *A61J 1/2096* (2013.01); *A61M 2039/1066* (2013.01); *A61M 2205/0216* (2013.01)

(58) Field of Classification Search

CPC ................ A61M 5/345; A61M 5/3134; A61M 2005/247; A61M 2005/2474; A61M 39/14; A61M 2039/1066; A61J 1/1412; A61J 1/201; A61J 1/2096

See application file for complete search history.

(56) References Cited

U.S. PATENT DOCUMENTS 6,003,566 A * 12/1999 Thibault ............... A61J 1/2096 604/416
2011/0022023 A1* 1/2011 Weitzel ..................... A61J 1/18 141/2
2014/0014210 A1* 1/2014 Cederschiold ...... A61M 5/3286 53/381.2
2018/0133396 A1* 5/2018 Mclaughlin ......... A61M 5/2466

OTHER PUBLICATIONS

Office Action (Communication pursuant to Article 94(3) EPC) issued by the European Patent Office on Sep. 3, 2024, in corresponding European Patent Application No. 20777927.3. (6 pages).

* cited by examiner

FIG. 6

| | Example 1 | | Comparative Example 1 |
|---|---|---|---|
| Compression Ratio (%) | 80 | 70 | 65 |
| Pressure Resistance | ○ | ○ | ○ |
| Puncturing Property | ○ | ○ | × |

| | Comparative Example 2 | Example 2 | |
|---|---|---|---|
| Compression Ratio (%) | 97 | 95 | 90 |
| Pressure Resistance | × | ○ | ○ |
| Puncturing Property | ○ | ○ | ○ |

CONNECTION STRUCTURE AND LIQUID MEDICINE ADMINISTRATION TOOL

CROSS-REFERENCES TO RELATED APPLICATIONS

This application is a continuation of International Patent Application No. PCT/JP2020/006454 filed on Feb. 19, 2020, which claims priority to Japanese Patent Application No. 2019-058721 filed on Mar. 26, 2019, the entire content of both of which is incorporated herein by reference.

FIELD OF THE INVENTION

The present invention generally relates to a connection structure of a medical container that discharges a liquid medicine while applying pressure to the liquid medicine inside, and a liquid medicine administration tool.

BACKGROUND DISCUSSION

A liquid medicine administration tool has conventionally been known that is mounted to a body of a patient to administer a liquid medicine. For example, Japanese Patent Application Publication No. 2010-131064 discloses a liquid medicine administration tool in which a syringe (medical container) and an actuator for operating a plunger thereof are contained in a housing. In this liquid medicine administration tool, a medicine is fed into a needle tube that subcutaneously punctures a patient via a tube mounted to a liquid medicine discharge part (tip) of a syringe.

Such a liquid medicine administration tool has a structure in which a screw-type female connector is provided on a tip of a syringe, and a male connector connected to an end part of a tube is screwed into the female connector to secure a flow path of a liquid medicine.

SUMMARY

In the liquid medicine administration tool, to enhance pressure resistance of the liquid medicine discharge part of the syringe, it is conceivable to provide an adapter on an outer periphery of the liquid medicine discharge part at the syringe tip and to have a luer taper structure in which a tube with a connector is connected to the adapter by screwing.

However, in fixing by a screw mechanism, a screw may gradually loosen during use. For this reason, there is a problem that the patient needs to regularly manage a degree of fastening between the connector and the adapter, which is complicated.

On the other hand, in a connection method in which an elastic sealing body including an elastic member is provided in the liquid medicine discharge part of the medical container and the elastic sealing body is punctured with a connection needle, loosening seen in a screw-type connector does not occur. For that reason, it is effective for continuously securing the flow path for a long time.

However, when the pressure of the liquid medicine is high, airtightness between the elastic sealing body and the connection needle or between the elastic sealing body and the liquid medicine discharge part of the medical container becomes insufficient, and liquid leakage may occur.

Thus, to improve the airtightness of the elastic sealing body, it is conceivable to increase filling pressure of the elastic sealing body at time of product production, but there is a problem that repulsive force of the elastic sealing body is lost due to heat of a sterilization process and change with time during storage, and it is not easy to increase the airtightness. In addition, when the filling pressure of the elastic sealing body is high, there is also a problem that puncturing with the connection needle becomes difficult.

Thus, there is a demand for a connection structure and a liquid medicine administration tool capable of easily puncturing an elastic sealing body with a connection needle while maintaining sufficient pressure resistance.

One aspect of the following disclosure is in a connection structure of a medical container including a liquid medicine containing part that contains a liquid medicine and a liquid medicine discharge part provided at a distal end of the liquid medicine containing part and discharging the liquid medicine. The connection structure comprises: a sealing member and a connector. The sealing member includes a mounting part to be mounted to the liquid medicine discharge part to cover an outside of the liquid medicine discharge part, an opening formed at a distal end part of the mounting part, and an elastic sealing body disposed in a space adjacent the opening so that the elastic sealing body is between the opening and the liquid medicine discharge part to seal the liquid medicine discharge part when the mounting part is mounted to the liquid medicine discharge part. The connector includes a connection needle configured to puncture the elastic sealing body and a needle hub that holds the connection needle, with the connector being mountable to the sealing member. The connector includes a push-in structure that compresses the elastic sealing body when the connector is mounted to the sealing member and the connection needle punctures the elastic sealing body. The push-in structure compresses the elastic sealing body in a range of a compression ratio B/A of 70% to 95% when the connector is mounted to the sealing member and the connection needle punctures the elastic sealing body, wherein A is a volume of the elastic sealing body before puncturing with the connection needle and B is a volume of the elastic sealing body after puncturing with the connection needle.

Another aspect of the following disclosure involves a liquid medicine administration tool including: a medical container including a liquid medicine containing part that contains a liquid medicine and a liquid medicine discharge part that discharges the liquid medicine; and a connection structure configured to be connected to the liquid medicine discharge part. The connection structure comprises a sealing member and a connector. The sealing member includes a mounting part mountable to the medical container to cover an outside of the liquid medicine discharge part, an opening formed in the mounting part in an extending direction of the liquid medicine discharge part when the mounting part is mounted to the medical container, and an elastic sealing body disposed in a space adjacent the opening to seal the liquid medicine discharge part when the mounting part is mounted to the medical container. The connector is mountable to the sealing member and has a connection needle that punctures the elastic sealing body when the connector is mounted to the sealing member, and a needle hub that holds the connection needle. The connector includes a push-in structure that compresses the elastic sealing body when the connector is mounted to the sealing member while the mounting part is mounted to the medical container and the connection needle punctures the elastic sealing body. The push-in structure compresses the elastic sealing body in a range of a compression ratio B/A of 70% to 95% when the connector is mounted to the sealing member while the mounting part is mounted to the medical container and when the connection needle punctures the elastic sealing body, wherein A is a volume of the elastic sealing body before puncturing with the connection needle is A and a volume of the elastic sealing body after puncturing with the connection needle is B According to the connection structure and the liquid medicine administration tool from the above viewpoint, the elastic sealing body exerts sufficient pressure resistance and airtightness can be maintained even when used in a flow path that requires a high pressure resistance.

Another aspect of the disclosure here involves a method comprising mounting a connector onto a sealing member that is mounted on a liquid medicine discharge part of a medical container. The medical container also includes a liquid medicine containing part having an interior that contains a liquid medicine, with the liquid medicine discharge part being at a distal end of the liquid medicine containing part. The sealing member includes: a mounting part that is mounted to the liquid medicine discharge part in covering relation to an outside of the liquid medicine discharge part; an opening at a distal end part of the mounting part, and an elastic sealing body positioned in a space between the opening and the liquid medicine discharge part to seal the liquid medicine discharge part. The connector includes a needle hub and a connection needle in which is located a flow path, with the connection needle being connected to and extending away from the needle hub. The mounting of the connector onto the sealing member includes puncturing the elastic sealing body with the connection needle so the flow path in the connection needle is in communication with the interior of the liquid medicine containing part to permit the liquid in the interior of the liquid medicine containing part to flow into the flow path and be discharged from the interior of the liquid medicine containing part. The the mounting of the connector onto the sealing member results in the elastic sealing body being compressed in a range of a compression ratio B/A of 70% to 95%, wherein A is a volume of the elastic sealing body before puncturing with the connection needle and B is a volume of the elastic sealing body after puncturing with the connection needle.

BRIEF DESCRIPTION OF THE DRAWINGS

FIG. 6 is a table showing evaluation results of pressure resistance and a puncturing property in connection structures of Example 1 and Comparative Example 1.

FIG. 10 is a table showing evaluation results of pressure resistance and a puncturing property in connection structures of Example 2 and Comparative Example 2.

DETAILED DESCRIPTION

Figure 1:
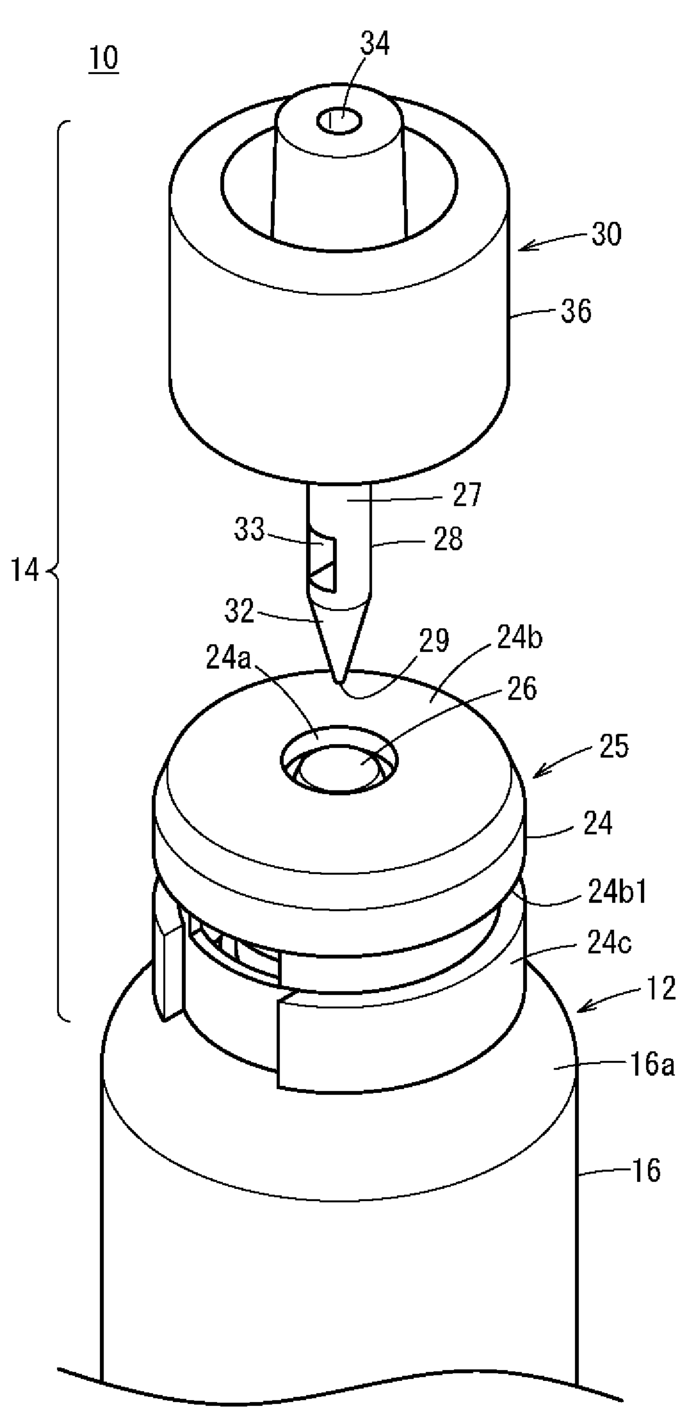
FIG. 1 is a perspective view illustrating a connection structure and a liquid medicine administration tool according to a first embodiment in a state before puncturing with a connection needle.

Hereinafter, preferred embodiments of the connection structure and liquid medicine administration tool will be described in detail with reference to the accompanying drawings. Dimensional ratios in the drawings may be exaggerated and different from actual ratios for convenience of description. In the following description, a direction from a liquid medicine containing part 16 of a medical container 12 toward connection needles 28 and 38 is referred to as a "distal end direction" or a "distal end side", and the opposite direction is referred to as a "proximal end direction" or a "proximal end side".

First Embodiment

As illustrated in FIG. 1, a liquid medicine administration tool 10 according to the present embodiment includes the medical container 12 that supplies a liquid medicine and a connection structure 14 mounted to the medical container 12. The medical container 12 illustrated is, for example, a syringe. The medical container 12 includes the liquid medicine containing part 16 that contains a liquid medicine on the proximal end side. The liquid medicine containing part 16 is formed in a cylindrical shape, and a containing chamber 18 (see FIG. 2) is formed therein. The liquid medicine containing part 16 and the containing chamber 18 extend in the axial direction.

Although not particularly illustrated, a gasket that liquid-tightly partitions the containing chamber 18 is provided on the proximal end side of the liquid medicine containing part 16. A pusher is joined to the proximal end side of the gasket. The pusher is operated by various driving means such as manual driving or electric driving, and is configured to pressurize the liquid medicine contained in the containing chamber 18 to a predetermined pressure. The liquid medicine administration tool 10 and the connection structure 14 are required to normally operate without causing liquid leakage, breakage, or the like even when the predetermined pressure (for example, about 600 kPa) acts on the liquid medicine in the containing chamber 18.

Figure 2:
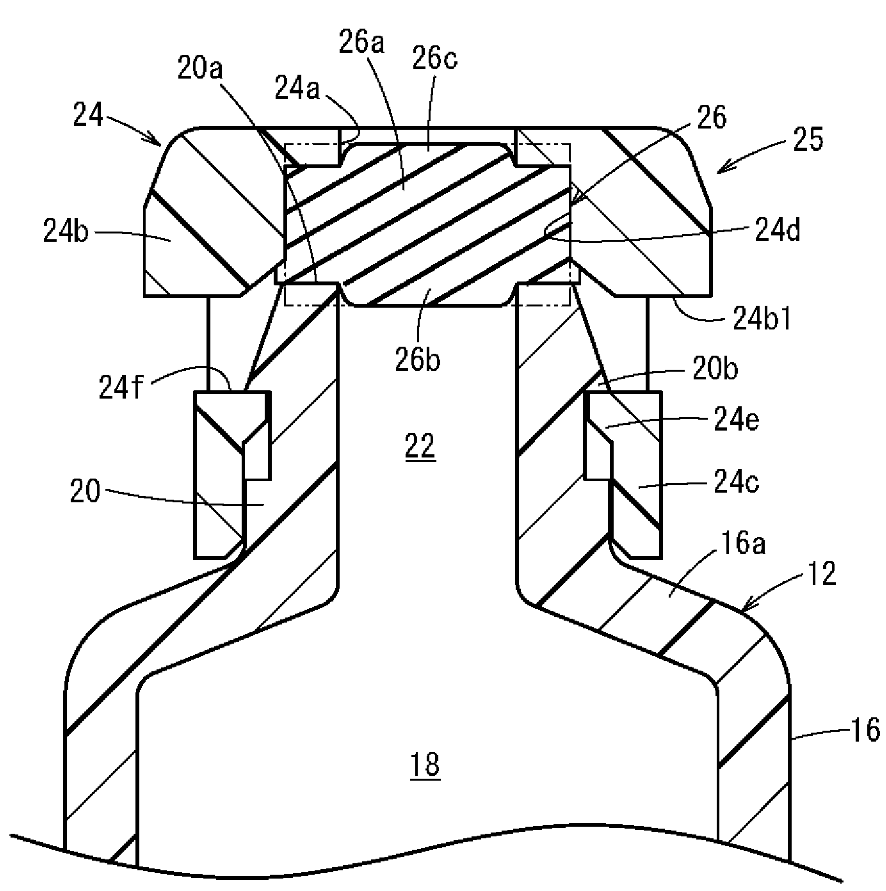
FIG. 2 is a cross-sectional view illustrating a liquid medicine discharge part and a sealing member of FIG. 1.

A reduced diameter part **16*a* having a reduced diameter is provided on the distal end side of the liquid medicine containing part 16. As illustrated in FIG. 2, a liquid medicine discharge part 20 that discharges the liquid medicine protrudes from the reduced diameter part 16*a* toward the axial direction distal end side. The liquid medicine discharge part 20 is formed in a cylindrical shape, and a liquid medicine flow path 22 communicating with the containing chamber 18 is formed along the central axis of the liquid medicine discharge part 20 inside the liquid medicine discharge part 20. The liquid medicine flow path 22 is opened at a distal end part 20*a* of the liquid medicine discharge part 20**.

As illustrated in FIG. 1, the connection structure 14 includes a sealing member 25 that is mounted to cover an outer periphery and the distal end part **20*a* of the liquid medicine discharge part 20 and seals the liquid medicine flow path 22 of the liquid medicine discharge part 20, and a connector 30 that punctures the sealing member 25. Among them, the sealing member 25 includes a mounting part 24** mounted to the outer periphery of the liquid medicine discharge part 20, an opening 24*a* formed in the mounting part 24, and an elastic sealing body 26 disposed in a space between the opening 24*a* and the liquid medicine discharge part 20, as illustrated in FIG. 2.

The mounting part 24 is a member formed in a bottomed cylindrical shape, and includes a side wall part 24*c* formed in a cylindrical shape and a distal end wall 24*b* formed on the distal end side of the side wall part 24*c* and extending in a radial direction inward. The side wall part 24*c* is disposed to cover the outside of the liquid medicine discharge part 20. The side wall part 24*c* is provided with a claw part 24*e* protruding inward. The claw part 24*e* is engageable with an engagement protrusion 20*b* protruding outward from the liquid medicine discharge part 20. The claw part 24*e* is engaged with the engagement protrusion 20*b* of the mounting part 24, whereby the mounting part 24 is fixed to the liquid medicine discharge part 20. A stepped part 24*b*1 for externally mounting the connector 30 is formed at a boundary between the distal end wall 24*b* and the side wall part 24*c*. The stepped part 24*b*1 is formed to protrude in the radial direction outward from and beyond the side wall part 24*c*. A window part 24*f* through which the engagement protrusion 20*b* passes is provided in a part in the circumferential direction of the side wall part 24*c*.

A containing recess 24*d* for containing the elastic sealing body 26 is formed inside the distal end wall 24*b*. The containing recess 24*d* is formed as a circular recess having an outer diameter substantially equal to an outer diameter of the distal end part 20*a* of the liquid medicine discharge part 20. When the mounting part 24 is mounted to the liquid medicine discharge part 20, the containing recess 24*d* is caused to form a columnar space having an outer diameter substantially equal to an outer diameter of the liquid medicine discharge part 20.

The opening 24*a* having a circular shape is formed in the distal end wall 24*b* near the central axis of the mounting part 24. The opening 24*a* penetrates the distal end wall 24*b* in the axial direction and communicates with the containing recess 24*d*. The opening 24*a* is formed to have an inner diameter substantially equal to an inner diameter of the liquid medicine flow path 22 of the liquid medicine discharge part 20, and is formed in an extending direction of the liquid medicine flow path 22.

The mounting part 24 is formed of, for example, a synthetic resin such as polyethylene, polypropylene, polycarbonate, polystyrene, and acrylic, or a metal material such as stainless steel, a titanium alloy, and an aluminum alloy.

The elastic sealing body 26 is formed of an elastic material such as a medical rubber material (for example, butyl rubber, isoprene rubber, butadiene rubber, and the like) or various elastomer materials. In a state before being assembled to the sealing member 25, the elastic sealing body 26 is formed in a disk shape (disk-shaped elastic sealing body 26) as indicated by a two-dot chain line in FIG. 2. An outer diameter of the elastic sealing body 26 is substantially the same as an inner diameter of the containing recess 24*d*. In addition, in the state before being assembled, a thickness (axial length) of the elastic sealing body 26 is, for example, about 20% larger than an axial dimension of the containing recess 24*d*.

The elastic sealing body 26 is assembled to the liquid medicine discharge part 20 together with the mounting part 24, in a state of being inserted into the containing recess 24*d*. That is, the elastic sealing body 26 is assembled to the liquid medicine discharge part 20 together with the mounting part 24 when the elastic sealing body 26 is positioned in the containing recess 24*d*. As a result, the elastic sealing body 26 is disposed in the space formed by the containing recess 24*d*, in a state of being compressed in the axial direction. A part compressed in the axial direction of the elastic sealing body 26 is in close contact with the containing recess 24*d* to constitute a main body part 26*a* having a disk shape (disk-shaped main body part 26*a*). In addition, a first protrusion 26*b* protrudes from the proximal end side of the elastic sealing body 26 and is inserted into or positioned in the liquid medicine flow path 22 of the liquid medicine discharge part 20, and a second protrusion 26*c* protrudes from the distal end side of the elastic sealing body 26 and is inserted into or positioned in the opening 24*a*.

The elastic sealing body 26 is compressed so that the thickness in the axial direction of the main body part 26*a* is about 80% of its thickness in the original state, and a gap between the mounting part 24 and the liquid medicine discharge part 20 is tightly filled, thereby liquid-tightly and air-tightly sealing the liquid medicine flow path 22 of the liquid medicine discharge part 20.

As illustrated in FIG. 1, the connector 30 includes the connection needle 28 having a needle tip 29 that is sharp, and a needle hub 36 that supports the connection needle 28. The connection needle 28 protrudes toward the proximal end side of the needle hub 36, and includes a puncturing part 32 whose outer diameter is reduced in a conical shape at a proximal end part thereof.

Figure 4:
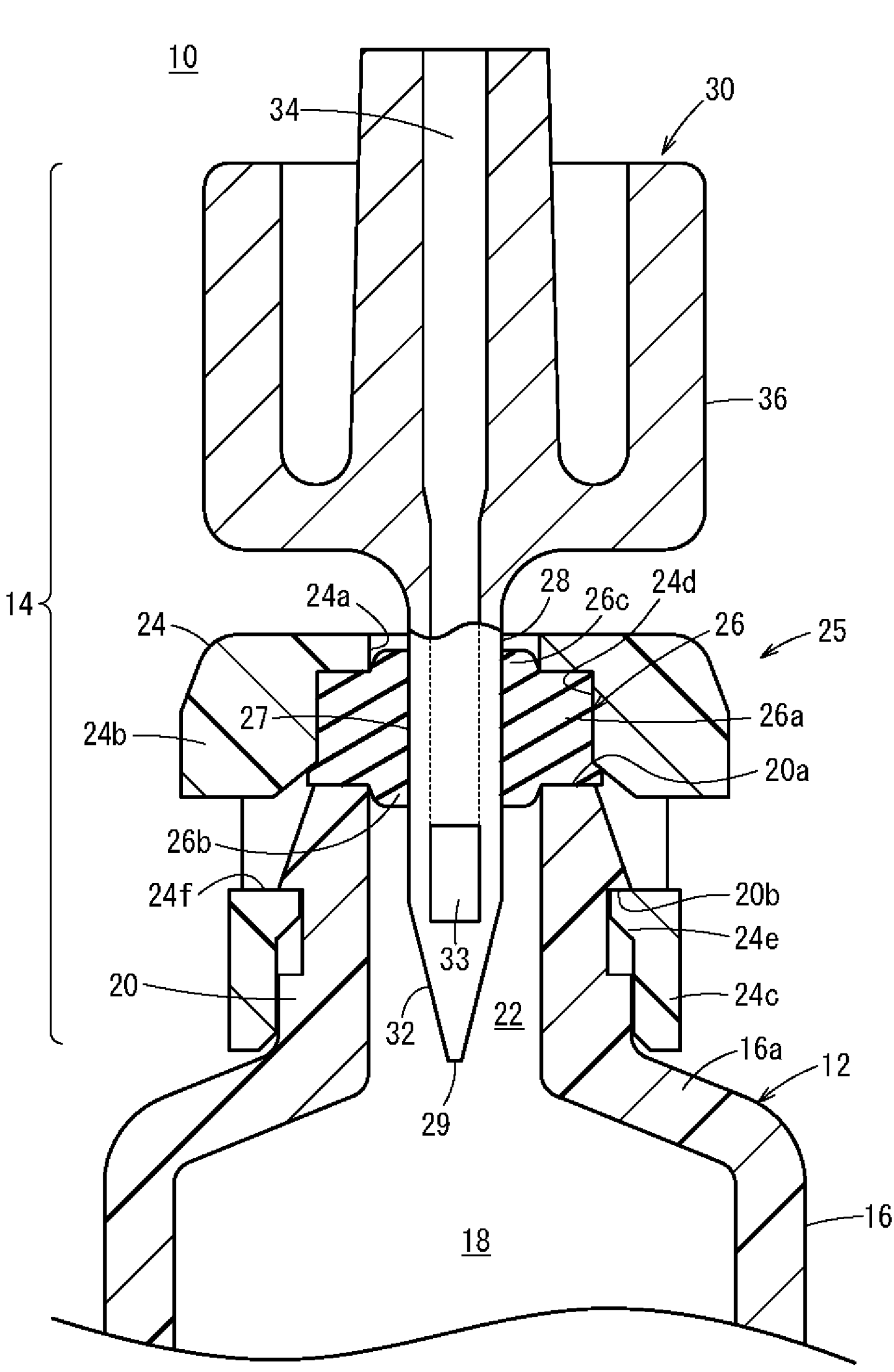
FIG. 4 is a cross-sectional view of the connection structure and the liquid medicine administration tool of FIG. 3.

As illustrated in FIG. 4, the connection needle 28 is formed in a hollow shape, and a flow path 34 is formed therein. The flow path 34 is opened at an opening 33 on a side part of the connection needle 28 that is out of or spaced from the needle tip 29 to prevent coring in which fragments of the elastic sealing body 26 enter the flow path 34 at the time of puncturing. The connection needle 28 of the present embodiment is formed to have an outer diameter larger than an outer diameter required to secure the flow path of the liquid medicine. The outer diameter of the connection needle 28 has a size capable of exerting predetermined pressure resistance between the connection needle 28 and the elastic sealing body 26 and between the elastic sealing body 26 and the sealing member 25 by compressing the elastic sealing body 26 in the radial direction outward when the elastic sealing body 26 is punctured. That is, the connection needle 28 constitutes a push-in structure 27 that presses the elastic sealing body 26 in the present embodiment. As shown in FIG. 4, when the connector 30 is mounted to the sealing member 25 so that the connection needle 27 punctures and passes through the elastic sealing body 26, the outer surface of the side wall part 24*c* is exposed (i.e., not covered by the connector 30).

Figure 3:
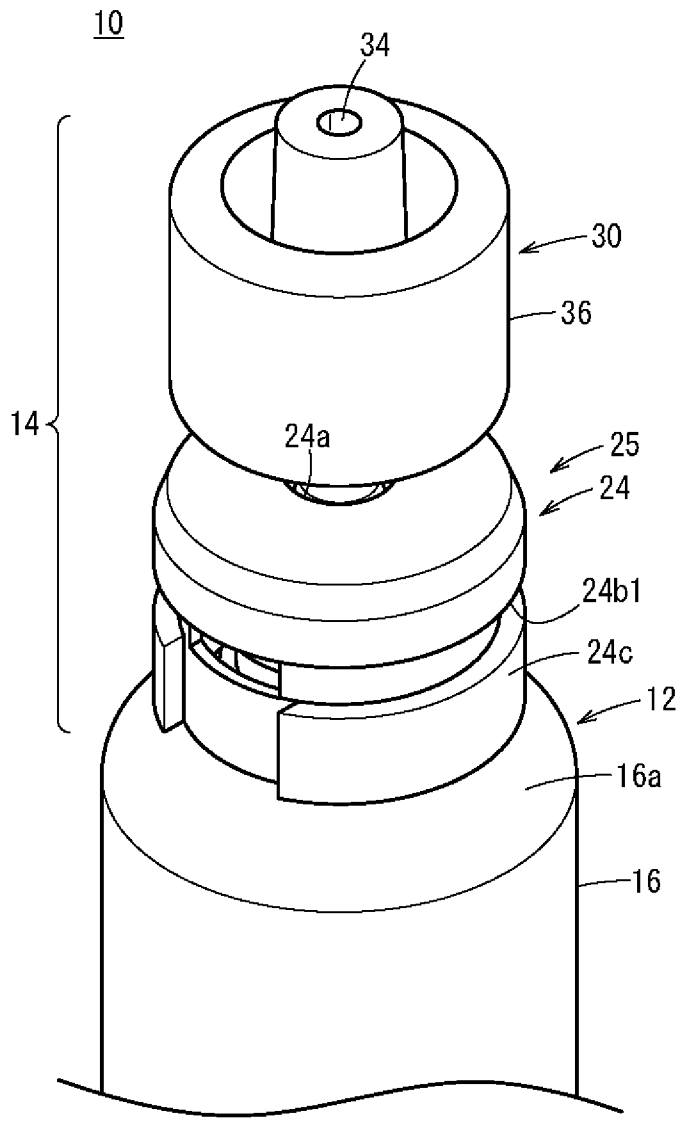
FIG. 3 is a perspective view illustrating the connection structure and the liquid medicine administration tool of FIG. 1 in a state after puncturing with the connection needle.

The needle hub 36 is formed integrally with the connection needle 28, and is formed in a cylindrical shape enlarged in diameter toward the outside of the connection needle 28. Although not particularly illustrated, a connection tube, a connector, or the like is mounted on the needle hub 36 side. As illustrated in FIG. 3, the connection structure 14 is used by pushing the connector 30 into the sealing member 25. At this time, as illustrated in FIG. 4, puncturing is performed such that the connection needle 28 pierces the elastic sealing body 26 from the opening 24*a* of the sealing member 25.

The elastic sealing body 26 is punctured with the connection needle 28, whereby the opening 33 of the flow path 34 of the connection needle 28 is disposed in the liquid medicine flow path 22 of the liquid medicine discharge part 20, and the flow path 34 communicates with the containing chamber 18. The liquid medicine can be discharged from the medical container 12 through the flow path 34 of the connection needle 28. When an internal pressure of the containing chamber 18 increases, there is a possibility that the liquid medicine leaks from a boundary between the liquid medicine discharge part 20 and the elastic sealing body 26 or a boundary part between the connection needle 28 and the elastic sealing body 26.

In the liquid medicine administration tool 10, after the sealing member 25 is assembled to the liquid medicine discharge part 20, autoclave sterilization of the medical container 12 is performed. At this time, since the liquid medicine administration tool 10 is exposed to a temperature of about 120° C., the elastic sealing body 26 may fit into a space between the sealing member 25 and the liquid medicine discharge part 20 and lose repulsive force. In addition, it is assumed that the liquid medicine administration tool 10 may be stored for about several months to one year after being manufactured and before being used, and during that time, the elastic sealing body 26 may lose its elastic force due to a temporal change. For that reason, in a conventional liquid medicine administration tool, the elastic sealing body cannot exert sufficient pressure resistance, and there has been a possibility that liquid leakage occurs when the internal pressure of the containing chamber increases.

On the other hand, in the liquid medicine administration tool 10 and the connection structure 14 of the present embodiment, the connection needle 28 is formed to be larger than a size required to secure the flow path of the liquid medicine. When the elastic sealing body 26 is punctured with the connection needle 28, the elastic sealing body 26 is compressed by a volume of a part where the connection needle 28 penetrates the elastic sealing body 26 in the thickness direction as illustrated by a shaded part V1 in FIG. 5, and a volume of the elastic sealing body 26 is reduced. That is, the elastic sealing body 26 is compressed outward in the radial direction by the connection needle 28, and pressure resistance of the elastic sealing body 26 can be exerted.

Example 1 and Comparative Example 1

Figure 5:
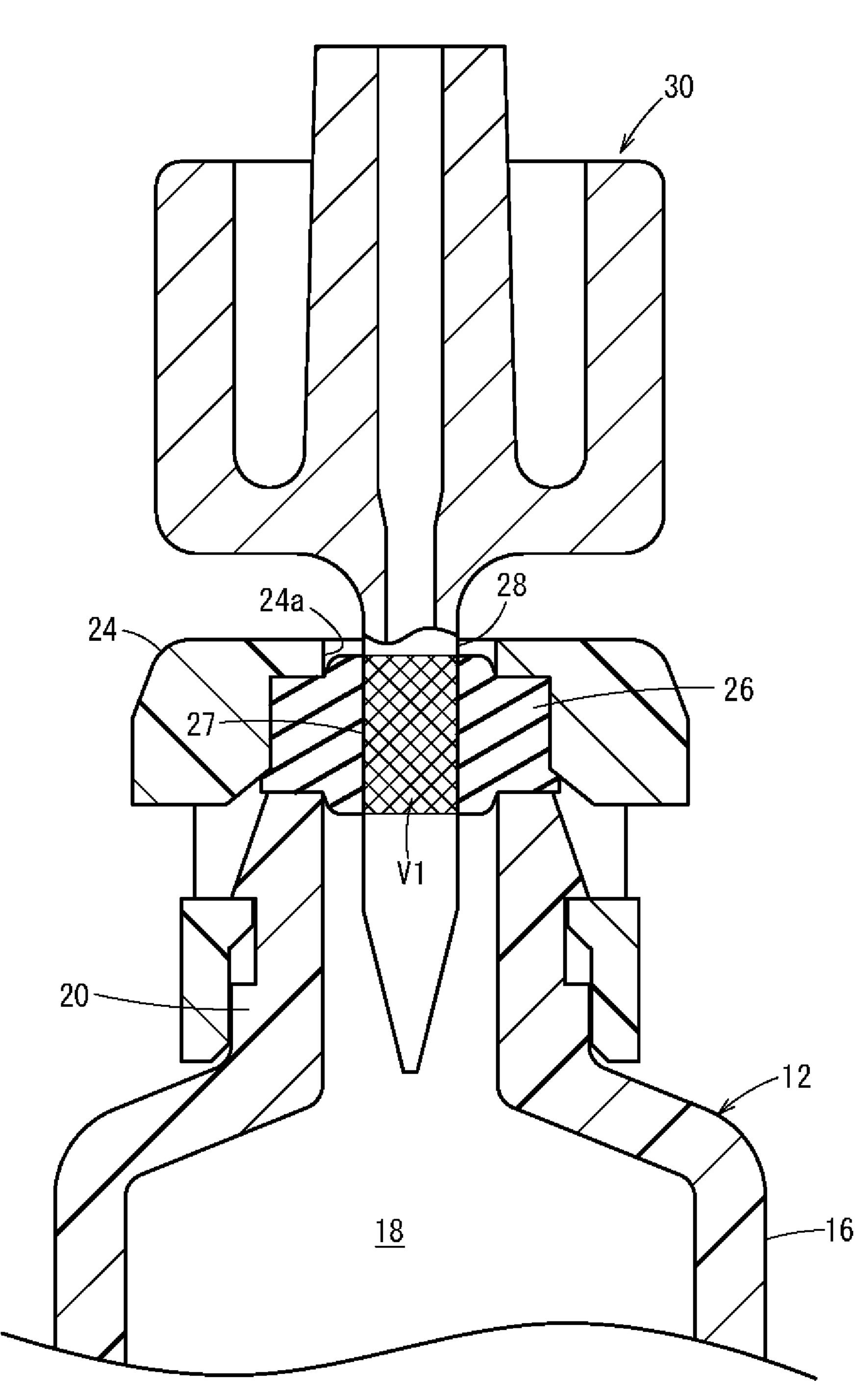
FIG. 5 is an explanatory diagram illustrating deformation of an elastic sealing body in the connection structure of FIG. 1.

In Example 1 and Comparative Example 1, the elastic sealing body 26 was punctured with the connection needle 28 illustrated in FIG. 5, and evaluation was performed on a preferred range of the compression ratio of the elastic sealing body 26. In the present specification, the compression ratio of the elastic sealing body 26 is a value obtained by dividing a volume B by a volume A (B/A) when the volume of the elastic sealing body 26 before puncturing with the connection needle 28 is A, and the volume of the elastic sealing body 26 after puncturing with the connection needle 28 is B. The volume B of the elastic sealing body 26 after puncturing is roughly the same as a value obtained by subtracting a volume of the shaded part V1 of the connection needle 28 of the part penetrating the elastic sealing body 26 from the volume A of the elastic sealing body 26 before puncturing.

In the present example, the connection needle 28 having a size at which the compression ratio of the elastic sealing body 26 was 80% and the connection needle 28 having a size at which the compression ratio of the elastic sealing body 26 was 70% were prepared. Then, a puncturing property was evaluated when the elastic sealing body 26 was punctured with these connection needles 28. In addition, the pressure resistance of the elastic sealing body 26 was evaluated by checking presence or absence of liquid leakage by applying a pressure of 600 KPa to the liquid medicine in the containing chamber 18 in a state where the elastic sealing body 26 was punctured with the connection needle 28.

On the other hand, in Comparative Example 1, the connection needle 28 having a size at which the compression ratio of the elastic sealing body 26 was 65% was prepared. Then, also in Comparative Example 1, the puncturing property and pressure resistance were evaluated.

Evaluation results of Example 1 and Comparative Example 1 are shown in FIG. 6. As illustrated in FIG. 6, in a range in which the size of the connection needle 28 is 80% to 70% in compression ratio, the elastic sealing body 26 could be easily punctured with the connection needle 28, and a good puncturing property was obtained (identified by "o" in FIG. 6). In addition, it was confirmed that liquid leakage did not occur even when the pressure of 600 KPa was applied to the liquid medicine in the containing chamber 18, and sufficient pressure resistance was obtained (identified by "o" in FIG. 6).

On the other hand, also in Comparative Example 1, it was confirmed that liquid leakage did not occur in the elastic sealing body 26, and sufficient pressure resistance was obtained (identified by "o" in FIG. 6). However, in Comparative Example 1, a large force was required to puncture the elastic sealing body 26, and a problem occurred in the puncturing property (identified by "x" in FIG. 6). That is, it has been found that in a range in which the compression ratio is less than or equal to 65%, a load is excessively applied to a peripheral member, such as displacement of the elastic sealing body 26 due to load input at the time of puncturing.

Thus, as in the present embodiment, as the push-in structure 27, when the outer diameter of the connection needle 28 is increased, it is preferable that the elastic sealing body 26 has a size in a range in which the compression ratio is greater than or equal to 70%. That is, the connection needle 28 should preferably have an outer diameter such that when the connection needle 28 is inserted into elastic sealing body 26 as shown in FIG. 5, the compression ratio of the elastic sealing body 26 is greater than or equal to 70%.

The liquid medicine administration tool 10 and the connection structure 14 of the present embodiment have the following effects.

The connection structure 14 relates to the connection structure 14 used for the medical container 12 including the liquid medicine containing part 16 that contains the liquid medicine and the liquid medicine discharge part 20 provided at the distal end of the liquid medicine containing part 16 and discharging the liquid medicine, and includes: the sealing member 25 including the mounting part 24 to be mounted to cover the outside of the liquid medicine discharge part 20, the opening 24*a* formed at the distal end part of the mounting part 24, and the elastic sealing body 26 disposed in the space between the opening 24*a* and the liquid medicine discharge part 20 and sealing the liquid medicine discharge part 20; and the connector 30 including the connection needle 28 that punctures the elastic sealing body 26, and the needle hub 36 that holds the connection needle 28, the connector 30 being mountable to the sealing member 25, in which the connector 30 has the push-in structure 27 that compresses the elastic sealing body 26 when the connection needle 28 punctures the elastic sealing body 26.

With the above configuration, even when the elastic sealing body 26 is fitted and loses its repulsive force, the elastic sealing body 26 is compressed immediately before use, and the pressure resistance of the elastic sealing body 26 can be recovered.

In the connection structure 14 described above, when the volume of the elastic sealing body 26 before puncturing with the connection needle 28 is A and the volume of the elastic sealing body 26 after puncturing with the connection needle 28 is B, the connection needle 28 constituting the push-in structure 27 compresses the elastic sealing body 26 in a range in which the compression ratio B/A is greater than or equal to 70%. With such a configuration, it is possible to achieve both the puncturing property of the connection needle 28 and securing the pressure resistance of the elastic sealing body 26.

In the connection structure 14 described above, the elastic sealing body 26 may be formed in a disk shape, the push-in structure 27 may include the connection needle 28 having a predetermined outer diameter with respect to the outer diameter of the elastic sealing body 26, and the push-in structure 27 (connection needle 28) may increase the compression ratio in the radial direction of the elastic sealing body 26. With such a configuration, the pressure resistance of the elastic sealing body 26 can be improved.

In the connection structure 14 described above, the volume A of the elastic sealing body 26 may be compressed more than the volume of the elastic sealing body 26 before being disposed in the gap between the opening 24*a* and the liquid medicine discharge part 20. As a result, since the elastic sealing body 26 is disposed in the gap between the opening 24*a* and the liquid medicine discharge part 20 without a gap, puncturing with the connection needle 28 is efficiently converted into compressive force of the elastic sealing body 26, and the pressure resistance of the elastic sealing body 26 can be reliably improved.

The liquid medicine administration tool 10 of the present embodiment includes: the medical container 12 including the liquid medicine containing part 16 that contains the liquid medicine and the liquid medicine discharge part 20 that discharges the liquid medicine; and the connection structure 14 connected to the liquid medicine discharge part 20. Then, the connection structure 14 of the liquid medicine administration tool 10 includes: a sealing member 25 including a mounting part 24 to be mounted to cover the outside of the liquid medicine discharge part 20, the opening 24*a* formed in the mounting part 24 in the extending direction of the liquid medicine discharge part 20, and the elastic sealing body 26 disposed in the space between the opening 24*a* and the liquid medicine discharge part 20 and sealing the liquid medicine discharge part 20; and the connector 30 including the connection needle 28 that punctures the elastic sealing body 26, and the needle hub 36 that holds the connection needle 28, in which the connector 30 has the push-in structure 27 that compresses the elastic sealing body 26 when the connection needle 28 punctures the elastic sealing body 26. As a result, the liquid medicine administration tool 10 is obtained that can be used without liquid leakage even when high pressure acts.

Second Embodiment

Figure 7:
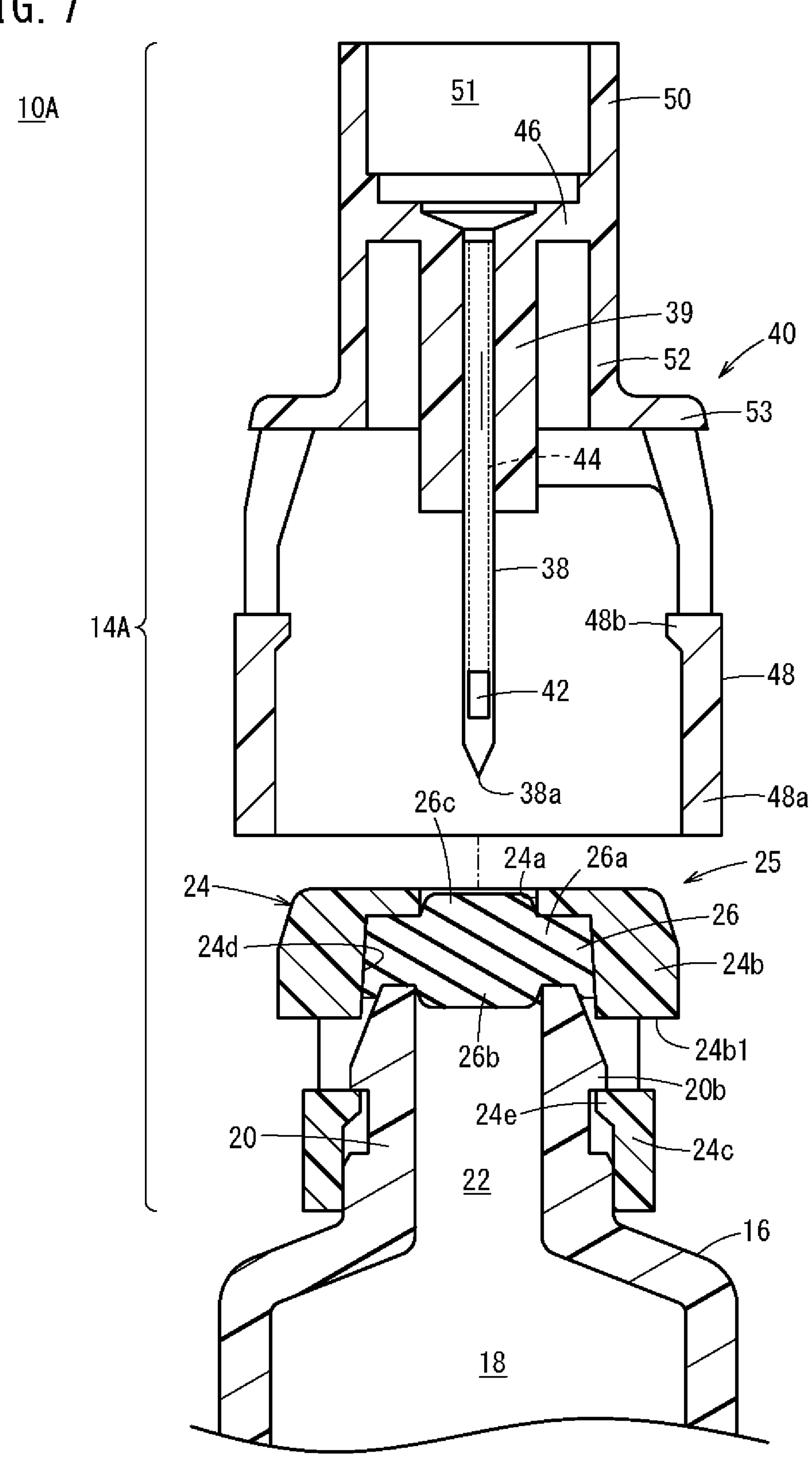
FIG. 7 is a cross-sectional view illustrating a connection structure and a liquid medicine administration tool according to a second embodiment in a state before puncturing with a connection needle.

As illustrated in FIG. 7, a liquid medicine administration tool 10A and a connection structure 14A of the present embodiment are different from the liquid medicine administration tool 10 and the connection structure 14 described with reference to FIGS. 1 to 5 in a connector 40. In the liquid medicine administration tool 10A and the connection structure 14A, components similar to those of the liquid medicine administration tool 10 and the connection structure 14 are denoted by the same reference numerals, and a detailed description of such features is not repeated.

The connector 40 includes a connection needle 38, a needle hub 50 that holds the connection needle 38, a protruding part 39 provided at a base part of the connection needle 38, and a guide wall 48 formed to surround the outside of the connection needle 38.

The connection needle 38 is made of, for example, a metal material such as stainless steel, a copper alloy, a titanium alloy, or an aluminum alloy, and a needle tip 38*a* that is sharp is formed at a proximal end part thereof. The inside of the connection needle 38 is formed in a hollow shape, and the hollow part extends in the axial direction to form a flow path 44. The flow path 44 is opened in an opening 42 on a side part of the connection needle 38 on the distal end side of the needle tip 38*a* to prevent coring when the elastic sealing body 26 is punctured.

Figure 8:
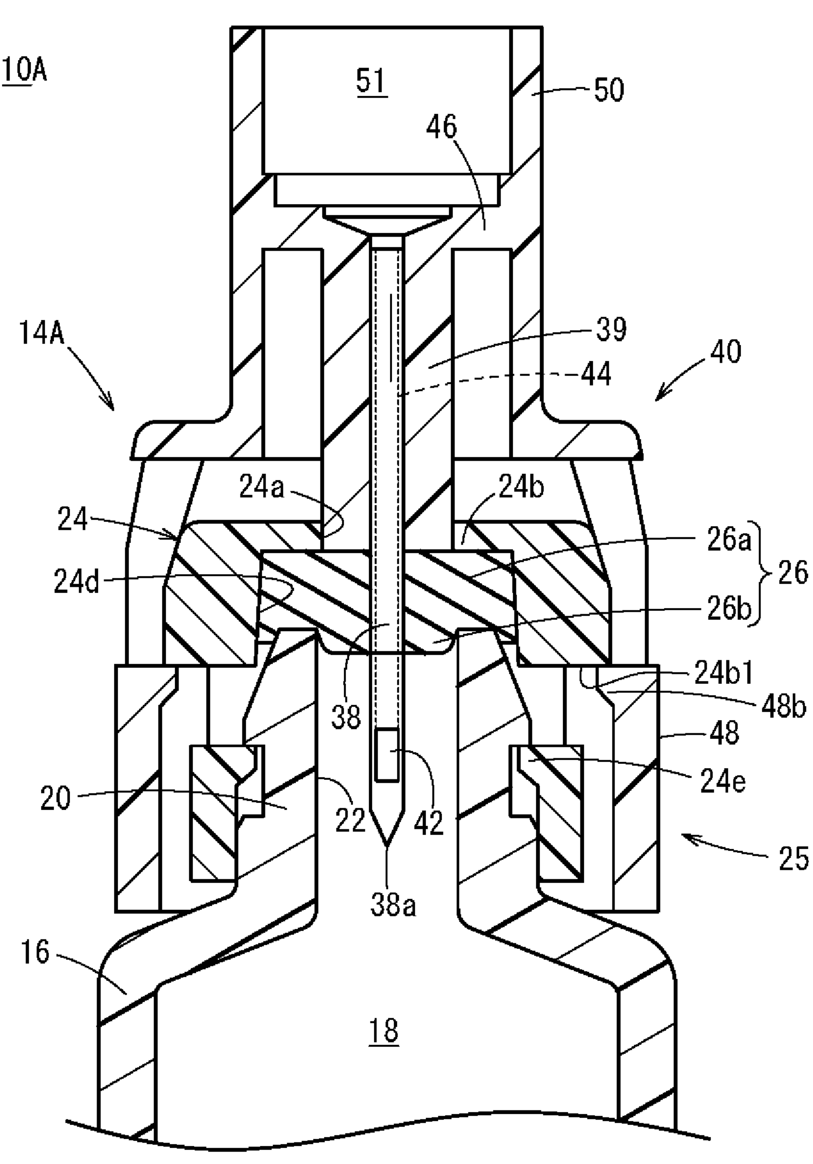
FIG. 8 is a cross-sectional view illustrating the connection structure and the liquid medicine administration tool of FIG. 7 in a state after puncturing with the connection needle.

The protruding part 39 is provided on the distal end side (base part) of the connection needle 38 to abut on an outer periphery of the connection needle 38. The protruding part 39 is formed in a cylindrical shape and protrudes from a partition wall 46 of the needle hub 50 to the axial direction proximal end side. As illustrated in FIG. 8, the protruding part 39 is a part that is inserted into the opening 24*a* of the mounting part 24 and presses the elastic sealing body 26 when the connector 40 is mounted on the sealing member 25, and constitutes a push-in structure in the present embodiment. The protruding part 39 is joined to the side part of the connection needle 38 with an adhesive or the like to hold the connection needle 38.

As illustrated in FIG. 7, a connection port 51 for connecting a connector or the like is formed on the distal end side of the partition wall 46. A cylindrical part 52 is formed to protrude in the proximal end direction, on the proximal end side of the partition wall 46. An enlarged diameter part 53 enlarged in outer diameter in a flange shape is provided at a proximal end part of the cylindrical part 52. The guide wall 48 is formed to extend in a cylindrical shape from the outer periphery of the enlarged outer diameter part 53 toward the proximal end side. An inner diameter of a proximal end part 48*a* of the guide wall 48 is formed to be substantially the same diameter as an outer diameter of the mounting part 24 of the sealing member 25. When the connector 40 is mounted to the sealing member 25, the guide wall 48 is fitted to the outer periphery of the mounting part 24 prior to the connection needle 38, and guides the connection needle 38 so that the connection needle 38 puncture the center of the elastic sealing body 26.

A lock piece 48*b* is formed to protrude inward, on an inner side part of the guide wall 48. The lock piece 48*b* is formed at a position engageable with the stepped part 24*b*1 of the mounting part 24. As illustrated in FIG. 8, when the connector 40 is pushed toward the proximal end side, the lock piece 48*b* is engaged with the stepped part 24*b*1, and the connector 40 is fixed to the sealing member 25 in a state of being urged toward the axial direction proximal end side.

In the present embodiment, the connection needle 38 is formed to have a diameter sufficient to secure a flow rate of the liquid medicine, and is formed to have an outer diameter smaller than that of the connection needle 28 described with reference to FIGS. 1 to 5. For that reason, the connection needle 38 can easily puncture the elastic sealing body 26. When the connector 40 is fixed to the sealing member 25, the protruding part 39 is pushed into the opening 24*a*, and the elastic sealing body 26 is compressed in the axial direction from the distal end side toward the proximal end side. By this compression, the elastic sealing body 26 is brought into close contact with the connection needle 38, the mounting part 24, and the liquid medicine discharge part 20 to exert pressure resistance.

Example 2 and Comparative Example 2

Figure 9:
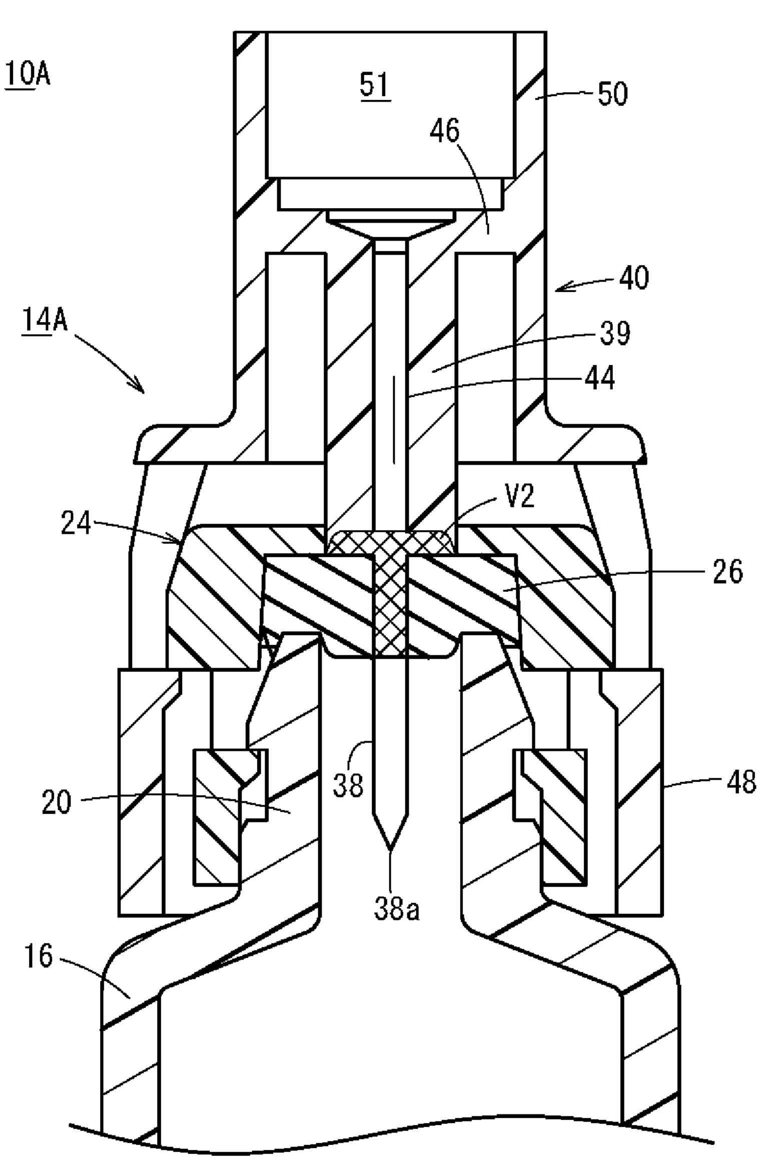
FIG. 9 is an explanatory diagram illustrating deformation of an elastic sealing body in the connection structure of FIG. 7.

In Example 2 and Comparative Example 2, the liquid medicine administration tool 10A and the connection structure 14A illustrated in FIG. 9 were prepared, and the puncturing property of the connection needle 38 and the pressure resistance of the elastic sealing body 26 were evaluated. The pressure resistance of the elastic sealing body 26 was evaluated based on presence or absence of liquid leakage under the condition that the internal pressure of the containing chamber 18 was 600 KPa as in Example 1.

In Example 2, the elastic sealing body 26 is compressed by a volume corresponding to a shaded part V2 in FIG. 9. Here, by preparing connectors whose protruding lengths in the proximal end direction of the protruding part 39 were varied, evaluation was performed for the connector 40 in which the compression ratio of the elastic sealing body 26 was set to 95% and the connector 40 in which the compression ratio of the elastic sealing body 26 was set to 90%.

In addition, in Comparative Example 2, a case was evaluated where only the connection needle 38 punctures the elastic sealing body 26 without pushing the protruding part 39 into the elastic sealing body 26. The compression ratio of the elastic sealing body 26 in Comparative Example 2 was 97%.

Results of Example 2 and Comparative Example 2 are shown in FIG. 10. As illustrated in the figure, in both the connector 40 having the compression ratio of 95% and the connector 40 having the compression ratio of 90% according to Example 2, the puncturing property was good, and the pressure resistance was also satisfactory (identified by "o" in FIG. 10).

On the other hand, in the connector 40 of Comparative Example 2, although a good result was obtained in terms of the puncturing property (identified by "o" in FIG. 10), the pressure resistance was insufficient, and liquid leakage occurred (identified by "x" in FIG. 10).

From the above results, it can be seen that in the connector 40 of the present embodiment, it is sufficient that the length of the protruding part 39 is in a range in which the compression ratio of the elastic sealing body 26 is less than or equal to 95%. That is the connector 40 should be configured so that the length of the protruding part 39 is in a range producing a compression ratio of the elastic sealing body 26 that is 95% or lower than 95%.

The liquid medicine administration tool 10A and the connection structure 14A of the present embodiment have the following effects.

The connection structure 14A of the present embodiment includes the push-in structure including the protruding part 39 formed to have an outer diameter larger than that of the connection needle 38 and protruding from the needle hub 50 toward the elastic sealing body 26, and the protruding part 39 increases the compression ratio in the axial direction of the elastic sealing body 26. According to such a connection structure 14A, it is possible to improve the pressure resistance of the elastic sealing body 26 while reducing the diameter of the connection needle 38 to improve the puncturing property.

In the connection structure 14A described above, when the volume of the elastic sealing body 26 before puncturing with the connection needle 38 is A and the volume of the elastic sealing body 26 after puncturing with the connection needle 38 is B, the protruding part 39 can be configured to compress the elastic sealing body 26 within a range in which the compression ratio B/A is less than or equal to 95%. By using the protruding part 39 capable of implementing such a compression ratio, the pressure resistance of the elastic sealing body 26 can be improved.

In the connection structure 14A described above, the connector 40 includes the guide wall 48 engageable with the mounting part 24, and the protruding part 39 is maintained in a state of being pushed in the axial direction toward the elastic sealing body 26 by engaging the connector 40 with the mounting part 24. As a result, a state can be maintained in which the protruding part 39 is pressed against the elastic sealing body 26, which is preferable.

In addition, the liquid medicine administration tool 10A of the present embodiment includes the connection structure 14A described above. As a result, the pressure resistance of the elastic sealing body 26 can be improved while the puncturing property of the connection needle 38 is improved.

In the above description, the connection structure and the liquid medicine administration tool have been described with reference to the preferred embodiments; however, the connection structure and the liquid medicine administration tool are not limited to the above-described embodiments. That is, the invention is not limited to the precise embodiments described, as various changes, modifications and equivalents can be effected by one skilled in the art without departing from the spirit and scope of the invention as defined in the accompanying claims. All such changes, modifications and equivalents which fall within the scope of the claims are expressly intended to be embraced by the claims. In the above description, the syringe has been described as an example of the medical container 12, but the present invention is not limited thereto, and the medical container 12 may be a flexible bag that contains the liquid medicine.

What is claimed is:

1. A connection structure of a medical container including a liquid medicine containing part that contains a liquid medicine and a liquid medicine discharge part provided at a distal end of the liquid medicine containing part and through which is to be discharged the liquid medicine, the connection structure comprising:

a sealing member including a mounting part to be mounted to the liquid medicine discharge part to cover an outside of the liquid medicine discharge part, an opening formed at a distal end part of the mounting part, and an elastic sealing body disposed in a space adjacent the opening so that the elastic sealing body is between the opening and the liquid medicine discharge part to seal the liquid medicine discharge part when the mounting part is mounted to the liquid medicine discharge part, the mounting part having an outwardly facing outer periphery;

a connector including a connection needle configured to puncture the elastic sealing body, a needle hub that holds the connection needle, and a guide wall that projects away from the needle hub and has an inner surface, the connector being mountable to the sealing member;

the mounting part being configured to be mounted on the liquid medicine discharge part before the connector is mounted to the sealing member, the mounting part including a side wall part configured to surround an outer periphery of the liquid medicine discharge part when the mounting part is mounted on the liquid medicine discharge part, the side wall part of the mounting part extending in a proximal direction away from the distal end part of the mounting part and terminating at a free end of the side wall part of the mounting part, the elastic sealing body being configured to be located between an open end of the liquid medicine discharge part and the mounting part when the mounting part is mounted on the liquid medicine discharge part, the guide wall having one end connected to the needle hub and an opposite free end, the guide wall including a lock piece that engages the proximally facing surface on a portion of the side wall part of the mounting part when the connector is mounted to the sealing member to fix the connector to the elastic sealing body in a manner urging the connector toward an axial direction proximal end side, the lock piece being located between the one end of the guide wall and the opposite free end of the guide wall, a portion of the guide wall between the lock piece and the opposite free end of the guide wall surrounding a part of the mounting part the connector including a push-in structure that compresses the elastic sealing body when the connector is mounted to the sealing member and the connection needle punctures the elastic sealing body;

the push-in structure compresses the elastic sealing body in a range of a compression ratio B/A of 70% to 95% when the connector is mounted to the sealing member and the connection needle punctures the elastic sealing body, wherein A is a volume of the elastic sealing body before puncturing with the connection needle and B is a volume of the elastic sealing body after puncturing with the connection needle;

the push-in structure including a protruding part possessing an outer diameter larger than an outer diameter of the connection needle, the protruding part having a first end connected to the needle hub, the protruding part also having an end portion that terminates at a second end of the protruding part opposite the first end of the protruding part, the protruding part protruding from the needle hub in a same direction as the connection needle, the protruding part increasing the compression ratio in an axial direction of the elastic sealing body when the connector is mounted to the sealing member and the connection needle punctures the elastic sealing body;

the end portion of the protruding part being in direct contact with an outer periphery of the connection needle;

the guide wall of the connector being fitted to and surrounding the outwardly facing outer periphery of the mounting part of the sealing member when the connector is mounted to the sealing member so that the inner surface of the guide wall faces toward and contacts the outwardly facing outer periphery of the mounting part when the connector is mounted to the sealing member, whereby the protruding part is pushed in the axial direction toward the elastic sealing body, and the side wall part comprising a claw part engageable with an engagement protrusion of the liquid medicine discharge part when the mounting part is mounted on the liquid medicine discharge part, the claw part of the side wall part of the mounting part being on a distal side of the free end of the side wall part of the mounting part, both the claw part of the side wall part of the mounting part and the free end of the side wall part of the mounting part being on a proximal side of the proximally facing surface of the side wall part of the mounting part.

2. The connection structure according to claim 1, wherein the push-in structure includes the connection needle having a predetermined outer diameter with respect to an outer diameter of the elastic sealing body, and the connection needle increases the compression ratio in a radial outward direction of the elastic sealing body when the connector is mounted to the sealing member and the connection needle punctures the elastic sealing body.

3. The connection structure according to claim 1, wherein the guide wall and the connection needle are configured so that when the connector is mounted to the sealing member, the guide wall is fitted to the outwardly facing outer periphery of the mounting part before the connection needle punctures the elastic sealing body and guides the connection needle towards toward the elastic body.

4. The connection structure according to claim 1, wherein the volume A of the elastic sealing body is compressed more than a volume of the elastic sealing body before being disposed in the space.

5. The connection structure according to claim 1, wherein the space in the mounting part is a disk-shaped space, and the elastic sealing body including a main body part positioned in the disk-shaped space before the connector is mounted to the sealing member and before the protruding part compresses the elastic sealing body, the elastic sealing body also including a first protrusion protruding axially from the main body part and positioned in the opening of the mounting part before the connector is mounted to the sealing member and before the protruding part compresses the elastic sealing body, and a second protrusion protruding axially from the main body part in a direction opposite the first protrusion.

6. The connection structure according to claim 1, wherein the side wall part has an outer surface that is exposed when the connector is mounted to the sealing member and the connection needle punctures and passes through the elastic sealing body.

7. The connection structure according to claim 1, wherein the push-in structure includes the connection needle, the connection needle possessing an outer diameter such that the compression ratio B/A is between 70% and 80%.

8. The connection structure according to claim 1, wherein the mounting part is mounted on the liquid medicine discharge part before the connector is mounted to the sealing member and before the protruding part compresses the elastic sealing body, the elastic sealing body being located between an open end of the liquid medicine discharge part and the mounting part, the protruding part being positionable in the opening at the distal end part of the mounting part to directly contact and compress the elastic sealing body when the connector is mounted to the sealing member and the connection needle punctures and passes through the elastic sealing body.

9. A liquid medicine administration tool comprising:

a medical container including a liquid medicine containing part that contains a liquid medicine and a liquid medicine discharge part through which the liquid medicine is discharged, the liquid medicine discharge part extending in an extending direction and having a central axis; and a connection structure connected to the liquid medicine discharge part, the connection structure including:

a sealing member including a mounting part mounted to the medical container and covering an outside of the liquid medicine discharge part, an opening formed in the mounting part in an extending direction of the liquid medicine discharge part, and an elastic sealing body disposed in a space between the opening and the liquid medicine discharge part and sealing the liquid medicine discharge part, the mounting part having an outwardly facing outer periphery, the elastic sealing body having one end surface that contacts and covers the liquid medicine discharge part, the elastic sealing body having an other end surface that faces in a direction away from the one end surface;

a connector mountable to the sealing member and including a connection needle that punctures the elastic sealing body and passes through the elastic sealing body when the connector is mounted to the sealing member, a needle hub that holds the connection needle and a guide wall that projects away from the needle hub and has an inner surface, the connection needle having a needle tip at an end of the connection needle opposite the needle hub, the connection needle also having an outer periphery;

the connector including a push-in structure that compresses the elastic sealing body when the connector is mounted to the sealing member and the connection needle punctures the elastic sealing body;

the push-in structure compresses the elastic sealing body in a range of a compression ratio B/A of 70% to 95% when the connector is mounted to the sealing member and when the connection needle punctures the elastic sealing body, wherein A is a volume of the elastic sealing body before puncturing with the connection needle is A and a volume of the elastic sealing body after puncturing with the connection needle is B; and the push-in structure including a protruding part possessing an outer diameter larger than an outer diameter of the connection needle, the protruding part having a first end connected to the needle hub, the protruding part also having an end portion that terminates at a second end of the protruding part opposite the first end of the protruding part, the protruding part protruding from the needle hub in a same direction as the connection needle, the second end of the protruding part being an end face of the protruding part that faces toward the needle tip of the connection needle, that extends radially away from the outer periphery of the connection needle and that is configured to contact the other end surface of the elastic sealing body when the connector is mounted to the sealing member and the connection needle punctures the elastic sealing body and passes through the elastic sealing body to compress the elastic sealing body in an axial direction of the elastic sealing body and thereby increase the compression ratio of the elastic sealing body in the axial direction, the elastic sealing body having a maximum thickness along the central axis;

the connection needle extending, in the same direction, beyond the second end of the protruding part before the connector is mounted to the sealing member by a distance greater than the maximum thickness of the elastic sealing body; and the guide wall of the connector being fitted to and surrounding the outwardly facing outer periphery of the mounting part of the sealing member when the connector is mounted to the sealing member so that the inner surface of the guide wall faces toward and contacts the outwardly facing outer periphery of the mounting part when the connector is mounted to the sealing member, whereby the protruding part is pushed in the axial direction toward the elastic sealing body.

10. The liquid medicine administration tool according to claim 9, wherein the medical container is a syringe, or a flexible bag.

11. The liquid medicine administration tool according to claim 9, wherein the connection needle and the guide wall extend away from the needle hub in a same extending direction, the guide wall extending in the extending direction beyond a tip end of the connection needle.

12. The liquid medicine administration tool according to claim 9, wherein the space adjacent the opening in the mounting part is a disk-shaped space, the elastic sealing body including a main body part positioned in the disk-shaped space before the connector is mounted to the sealing member and before the protruding part compresses the elastic sealing body, the elastic sealing body also including a first protrusion protruding axially from the main body part and positioned in the opening before the connector is mounted to the sealing member and before the protruding part compresses the elastic sealing body, and a second protrusion protruding axially from the main body part in a direction opposite the first protrusion.

13. The liquid medicine administration tool according to claim 9, wherein the push-in structure includes the connection needle, the connection needle possessing an outer diameter sufficient so that the compression ratio B/A is between 70% and 80%.

14. The liquid medicine administration tool according to claim 9, wherein mounting part is mounted on the liquid medicine discharge part before the connector is mounted to the sealing member, the mounting part including a portion surrounding an outer periphery of the liquid medicine discharge part before the connector is mounted to the sealing member, the protruding part being movable toward the mounting part when the connector is mounted to the sealing member and being positionable in the opening at the distal end part of the mounting part to directly contact and compress the elastic sealing body when the connector is mounted to the sealing member and the connection needle punctures and passes through the elastic sealing body.

15. A method comprising:

mounting a connector onto a sealing member that is mounted on a liquid medicine discharge part of a medical container, the medical container also including a liquid medicine containing part having an interior that contains a liquid medicine, the liquid medicine discharge part being at a distal end of the liquid medicine containing part;

the sealing member including: a mounting part that is mounted to the liquid medicine discharge part in covering relation to an outside of the liquid medicine discharge part, the mounting part having an outwardly facing outer periphery; an opening at a distal end part of the mounting part; and an elastic sealing body positioned in a space between the opening and the liquid medicine discharge part to seal the liquid medicine discharge part, the elastic sealing body having one end surface that contacts and covers the liquid medicine discharge and an other end surface that faces in a direction away from the one end surface;

the connector including: a needle hub; a connection needle in which is located a flow path, the connection needle being connected to and extending away from the needle hub, the connection needle having a needle tip at an end of the connection needle opposite the needle hub; a protruding part possessing an outer diameter larger than an outer diameter of the connection needle, having a first end connected to the needle hub, having an end portion that terminates at a second end of the protruding part opposite the first end of the protruding part, and protruding from the needle hub in a same direction as the connection needle, the second end of the protruding part being an end face of the protruding part that faces toward the needle tip of the connection needle and that extends away from the outer periphery of the connection needle; and a guide wall that projects away from the needle hub and has an inner surface;

the mounting of the connector onto the sealing member including fitting the guide wall of the connector to the outwardly facing outer periphery of the mounting part so that the inner surface of the guide wall faces toward and contacts the outwardly facing outer periphery of the mounting part, while the protruding part of the connector is pushed in an axial direction toward the elastic sealing body;

the mounting of the connector onto the sealing member also including puncturing the elastic sealing body with the connection needle so the connection needle passes through the elastic sealing body and so that the flow path in the connection needle is in communication with the interior of the liquid medicine containing part to permit the liquid in the interior of the liquid medicine containing part to flow into the flow path and be discharged from the interior of the liquid medicine containing part; and the end face at the second end of the protruding part contacting the other end surface of the elastic sealing body during the mounting of the connector onto the sealing member and being in contact with the other end surface of the elastic sealing body when the flow path in the connection needle is in communication with the interior of the liquid medicine containing part so that the elastic sealing body is compressed by the second end face of the protruding part resulting in the elastic sealing body being compressed in a range of a compression ratio B/A of 70% to 95%, wherein A is a volume of the elastic sealing body before puncturing with the connection needle and B is a volume of the elastic sealing body after puncturing with the connection needle, the protruding part increasing the compression ratio in the axial direction of the elastic sealing body by virtue of the end face at the second end of the protruding part contacting the other end surface of the elastic sealing body during the mounting of the connector onto the sealing member, the connection needle passing though the elastic body and being in communication with the interior of the liquid medicine containing part before the protruding part increases the compression ratio of the elastic sealing body.

16. The method according to claim 15, wherein the protruding part is located in the opening at the distal end part of the mounting part and directly contacts and compresses the elastic sealing body during the mounting of the connector onto the sealing member to compress the elastic sealing body within the compression ratio of 90% to 95%.

17. The method according to claim 15, wherein the connection needle has an outer diameter with respect to an outer diameter of the elastic sealing body such that as the connection needle punctures the elastic sealing body, the connection needle compresses the elastic sealing body in a radial outward direction to result in the compression ratio of 70% to 80%.

18. The connection structure according to claim 1, wherein mounting part is mounted to the medical container before the connector is mounted to the sealing member, the guide wall including an inwardly directed lock piece that engages a stepped part of the mounting part when the connector is mounted to the sealing member to fix the connector to the elastic sealing body, the stepped part of the mounting part being positioned in surrounding relation to a part of an outer periphery of the liquid medicine discharge part.

19. The connection structure according to claim 1, wherein the mounting part is mounted on the liquid medicine discharge part before the connector is mounted to the sealing member and before the connection needle punctures the elastic sealing body so that a portion of the mounting part surrounds an outer periphery of the liquid medicine discharge part and so that the elastic sealing body is held between an open end of the liquid medicine discharge part and the mounting part while a portion of the elastic sealing body spans the opening at the distal end part of the mounting part, the connector being movable toward the mounting part that is mounted on the liquid medicine discharge part to position the protruding part in the opening at the distal end part of the mounting part so that the protruding part directly contacts the elastic sealing body.

* * * * *